United States Patent [19]
Wagner et al.

[11] 3,976,622

[45] Aug. 24, 1976

[54] PROCESS FOR THE PRODUCTION OF POLYISOCYANATES WITH A BIURET STRUCTURE

[75] Inventors: Kuno Wagner; Johannes Eimer; Joachim Zirner, all of Leverkusen; Rainer Raab, Odenthal; Dietrich Liebsch, Leverkusen, all of Germany

[73] Assignee: Bayer Aktiengesellschaft, Leverkusen, Germany

[22] Filed: May 19, 1975

[21] Appl. No.: 578,557

Related U.S. Application Data

[62] Division of Ser. No. 441,778, Feb. 12, 1974, Pat. No. 3,903,127.

[30] Foreign Application Priority Data

Feb. 17, 1973  Germany............................ 2308015

[52] U.S. Cl...................... 260/77.5 AT; 260/75 NT

[51] Int. Cl.$^2$......................................... C08G 18/79
[58] Field of Search................. 260/77.5 AT, 75 NT

[56] References Cited
UNITED STATES PATENTS

| | | | |
|---|---|---|---|
| 3,350,438 | 10/1967 | Hennig....................... | 260/75 NT X |
| 3,591,560 | 7/1971 | Wagner et al.............. | 260/75 NT X |
| 3,684,771 | 8/1972 | Braun........................ | 260/77.5 AT X |
| 3,793,268 | 2/1974 | Dietrich et al. .......... | 260/77.5 AT X |

*Primary Examiner*—Lewis T. Jacobs
*Assistant Examiner*—S. M. Person
*Attorney, Agent, or Firm*—Joseph C. Gil; Gene Harsh

[57] ABSTRACT

Comparatively low viscosity biuret containing polyisocyanates are produced by reacting diisocyanates and biuretizing agents in proportions corresponding to a molar ratio of diisocyanate to monofunctional biuretizing agent of at least 11 : 1.

5 Claims, No Drawings

PROCESS FOR THE PRODUCTION OF POLYISOCYANATES WITH A BIURET STRUCTURE

This is a division of application Ser. No. 441,778, filed Feb. 12, 1974, now U.S. Pat. No. 3,903,127.

Processes for the production of polyisocyanates with biuret structures are already known, for example according to U.S. Pat. No. 3,124,605, polyisocyanates with a biuret structure are produced by reacting water with at least three mols of an organic diisocyanate. In the examples given in this U.S. Patent, the proportions used are preferably 3.4 to 5 mols of diisocyanate to 1 mol of water and the products obtained after removal of the excess diisocyanate are viscous liquids or solid resins consisting of polyisocyanate mixtures with a biuret structure. U.S. Pat. No. 3,358,010 discloses a process for the production of polyisocyanates with a biuret structure by reacting at least 2.5 mols of an aliphatic or cycloaliphatic diisocyanate with 1 mol of a monohydric tertiary alcohol. The polyisocyanates with biuret structures obtained by the process of this patent are also viscous liquids. The biuret polyisocyanates obtained according to German Offenlegungsschrift No. 1,931,055 are solid or resinous products of more or less viscous oils.

The polyisocyanates with biuret structures which can be obtained by these processes are complex mixtures which, in addition to biuret triisocyanates, contain higher homologues as well as polyisocyanates which contain urea groups. Biuret polyisocyanates which can be obtained from hexamethylene diisocyanate by the known processes of the art consist, as can be determined by fractional distillation with solvent mixtures of cyclohexane and ethyl acetate, of mixtures of a. 45 – 65 percent by weight of a triisocyanate of the formula

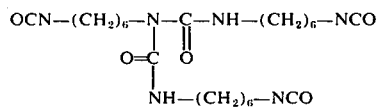

b. 20 – 35 percent by weight of tetra- and/or penta-isocyanate with biuret groups, and
c. 15 – 20 percent by weight of polyisocyanates with urea groups as represented by the following formula:

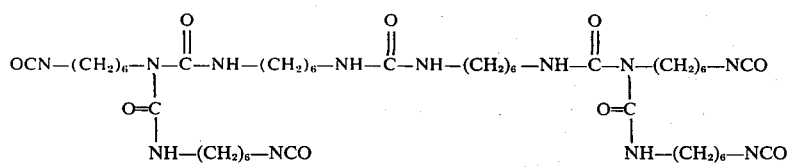

or higher molecular weight polyisocyanates with urea groups.

The high viscosity of the biuret polyisocyanates obtained by the known processes of the art is mainly due to the high proportion in them of the polyisocyanates mentioned under (b) and (c). Apart from increasing the viscosity, the polyisocyanates mentioned under (c) have the undesirable property of tending to separate them from dilute solutions of biuret polyisocyanate mixtures which have a solids content of 10 to 20 percent by weight so that opaque, cloudy solutions with a ground deposit are obtained. It follows that the biuret polyisocyanates of the known art, especially those based on aliphatic diisocyanates, are not always suitable for use as binder components in dilute lacquer solutions used for spraying in spite of their known advantages such as, in particular, their light-fastness and the fact that they are physiologically harmless.

The relatively high viscosity of the biuret polyisocyanates of the known art, which is generally above 10,000 cP at 20°C even in the case of biuret polyisocyanates prepared from aliphatic or cycloaliphatic diisocyanates, moreover prevents the preparation of solvent-free single component or two-component polyurethane lacquers which can easily be applied but it is precisely such solvent-free lacquer systems which are of increasing commercial importance in view of the desirability of preventing environmental pollution.

It is, therefore, an object of this invention to provide a process for the production of biuret polyisocyanates which are more easily diluted and have a substantially lower viscosity as well as having an improved capacity for taking up pigments.

It has surprisingly been found that this problem can be solved if the known reaction of organic diisocyanates with reactants which lead to biuret formation is carried out with a large excess of isocyanate.

This invention concerns a process for the production of polyisocyanates with a biuret structure which have a maximum viscosity of about 50,000 cP at 20°C by reacting excess quantities of organic diisocyanates with biuretizing agents at about 60° to about 250°C, optionally in the presence of catalysts and/or other auxiliary agents and additives, followed by the removal of excess, unreacted diisocyanate, characterized in that the organic diisocyanates and biuretizing agents are used in proportions corresponding to a molar ratio of diisocyanate to monofunctional biuretizing agent of at least 11 : 1.

The invention also relates to the biuret polyisocyanates obtainable by this process and to their use as isocyanate components for the production of polyurethane resins by the isocyanate polyaddition process.

By biuretizing agents are meant in this context chemical compounds which react with organic isocyanates at elevated temperatures to form biurets. Monofunctional biuretizing agents are compounds which, when reacted stoichiometrically in a molar concentration, convert 3 mols of isocyanate groups into one biuret group. Water and methylamine are typical examples of monofunctional biuretizing agents. For example, the monofunctional biuretizing agent, methylamine, reacts in a molar concentration with 3 mols of monoisocyanate to form the corresponding biuret according to the following equation:

3 R—NCO + CH₃—NH₂ → R—NH—CO—N—R + CH₃—NCO

An example of a typical difunctional biuretizing agent is 1,4-bis-(dimethylhydroxymethyl)-benzene which is used in Example 7, below. Even when used in only a half molar concentration it reacts stoichiometrically to convert three isocyanate groups into one biuret group.

It is surprising to find that, by the process according to the invention, biuret polyisocyanates with a substantially reduced viscosity can be obtained by carrying out the known biuretizing reaction with a high excess of diisocyanate, since the presence of a large excess of diisocyanate would, a priori, be expected to produce exactly the opposite result, namely the production of biuret polyisocyanates with an exceptionally high viscosity because the presence of a large quantity of diisocyanates would be expected to result in the formation of higher homologues, which would increase the viscosity, as illustrated by the following equations in which tris-(isocyanato hexyl)-biuret is used as the example:

ployed in rotary or thin layer evaporators for removing the diisocyanate excess and even when adding catalysts for accelerating the biuretization reaction.

The increased concentration of triisocyanatobiuret in the biuret polyisocyanates obtained by the process according to the invention which is in any case higher than 65 % by weight preferably within the range of 75 to 95 % by weight is accompanied by a substantial reduction in the viscosity of the products compared with the corresponding products obtained by the processes of the known art. In particular, the process according to the invention makes it possible to produce biuret polyisocyanates based on hexamethylene diisocyanate with viscosities substantially below about 4000 cP/20°C.

Any organic diisocyanates can be used in the process according to the invention, but diisocyanates with aliphatically bound isocyanate groups are preferred. The following are examples of such aliphatic, cycloaliphatic

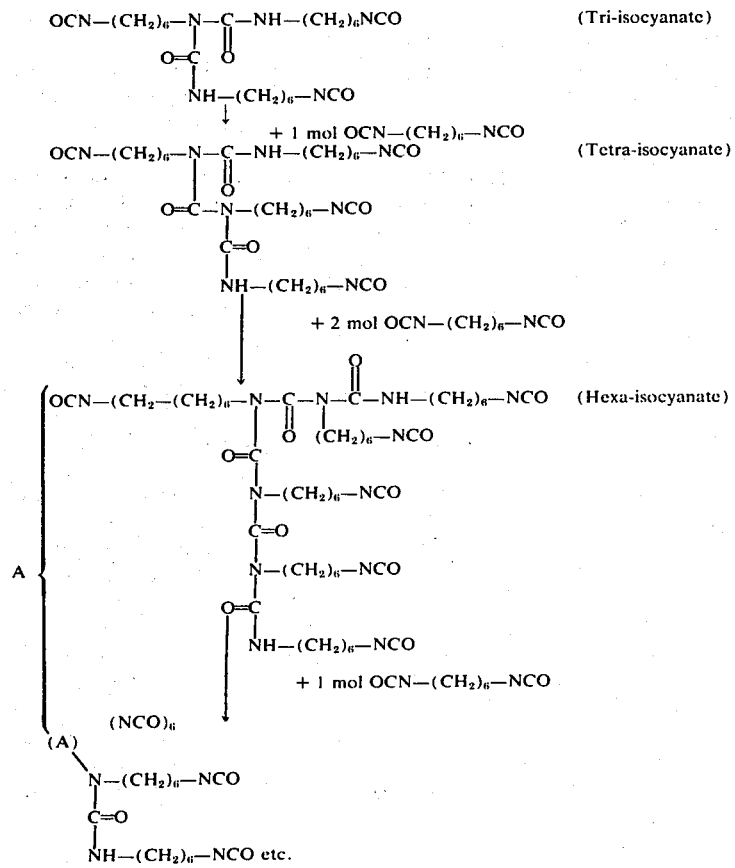

The surprising discovery has been made, however, that far from having this expected result, the presence of a large diisocyanate excess suppresses the formation of the higher homologues as well as suppressing the formation of polyisocyanates with urea groups mentioned under (c), so that the biuret polyisocyanates obtained by the process according to the invention contain a higher concentration of triisocyanato-biuret than the products obtained by the known processes of the art. This unexpected finding can be confirmed even when using relatively high temperatures of about 160° to 170°C which are the temperatures preferably emor araliphatic diisocyanates: Tetramethylene diisocyanate, pentamethylene diisocyanate, hexamethylene diisocyanate, cyclopentylene-1,3-diisocyanate, cyclohexylene-1,4-diisocyanate, cyclohexylene-1,2-diisocyanate, hexahydroxylylene diisocyanate, dicyclohexyl-4,4'-diisocyanate, 1,2-di-(isocyanatomethyl)-cyclobutane,1,3-bis-(isocyanatopropoxy)-2,2-dimethylpropane, 1,3-bis-(isocyanatopropyl)-2-methyl-2-propylpropane, 1-methyl-2,4-diisocyanatocyclohexane, 1-methyl-2,6-diisocyanatocyclohexane, bis-(4-isocyanatocyclohexyl)-methane, 1,4-diisocyanatocyclohexane and 1,3-diisocyanatocyclohexane, m- and p-xylylenediisocyanate, 3,3,5-trimethyl-5-isocyanatomethyl-cyclohexylisocyanate and 2,6-diisocyanatecaproic acid ester as well as the β-isocyanatoethylester and γ-isocyanatopropylester of isocyanatocaproic acid.

The following aliphatic, cycloaliphatic and araliphatic diisocyanates are preferred:

Hexamethylene diisocyanate, the isomeric mixture of 1-methyl-2,4-diisocyanato-cyclohexane and 1-methyl-2,6-diisocyanatocyclohexane, bis-(4-isocyanato-cyclohexyl)-methane, m- and p-xylylene diisocyanate, 3,3,5-trimethyl-5-isocyanatomethyl-cyclohexylisocyanate, methyl-substituted hexamethylene- and pentamethylene-diisocyanate, 2,6-diisocyanatocaproic acid ester and aliphatic diisocyanates which contain ether groups, such as 1,3-bis-(γ-isocyanatopropoxy)-2,2-dimethylpropane, 1,3-bis-(γ-isocyanatopropoxy)-2-methyl-2-propylpropane and α, ω-bis-isocyanatoethyl fumaric acid ester. The most suitable diisocyanate for the process according to the invention is hexamethylene diisocyanate.

If desired, aromatic diisocyanates can, of course, also be included in the process according to the invention if the products are not required to be lightfast and they can, of course, also be used exclusively as the only diisocyanates. The polyisocyanates with biuret structure obtained from these diisocyanates by the process according to the invention have a lower softening point and lower melt viscosity than the products which can be produced by the known processes.

The following are examples of suitable aromatic diisocyanates: 1-Methylbenzene-2,4-diisocyanate, 1-methyl-benzene-2,6-diisocyanate, commercial tolylene diisocyanate mixtures, m- and p-phenylene diisocyanate, naphthylene diisocyanate diphenylmethane diisocyanates, diisopropyl and triisopropyl benzene diisocyanates, 1-(isocyanatophenyl)- ethyl isocyanate and diisocyanates substituted with various substituents such as alkoxy or nitro groups or chlorine or bromine. Addition products of diisocyanates with subequivalent quantities of dihydroxy compounds such as butanediol or neopentylglycol are also suitable for the production of modified biurets. Mixtures of various polyisocyanates can also be used for biuret formation. Diphenylmethane diisocyanates which contain carbodiimide groups, e.g. those prepared according to U.S. Pat. No. 3,152,162, are also eminently suitable for biuret formation. Diisocyanates containing semicarbazide groups prepared according to U.S. Pat. No. 3,647,848 from asymmetrically disubstituted hydrazines are also suitable and constitute excellent antioxidants, stabilizers against discoloration in the heat and age resisters.

The biuretizing agents used in the process according to the invention can be any chemical compounds which make it possible to convert organic isocyanates into the corresponding biurets at elevated temperatures. If organic compounds are used as biuretizing agents in the process according to the invention, those substituents in the biuretizing agent which are inert in the biuretization reaction, for example methylamine in the above example, advantageously do not form a constituent of the products according to the invention. The following are examples of suitable biuretizing agents for the process according to the invention: Water, compounds which contain water as adduct such as in particular salts which contain water of crystallisation, organic compounds which split off water, e.g. organic dicarboxylic acids which tend to anhydride formation such as maleic acid or phthalic acid, tertiary alcohols such as tertiary butanol and tertiary amyl alcohol or 1,4-bis-(dimethyl-hydroxymethyl)-benzene, which has already been mentioned above, formic acid, primary aliphatic amines preferably containing not more than 6 carbon atoms, e.g. methylamine, ethylamine, butylamine, allylamine or hexylamine, sulphuric acid, N,N'-disubstituted ureas in which the substituents are preferably hydrocarbon groups with not more than 6 carbon atoms, e.g. N,N'-dimethyl-urea, N-methyl-N'-cyclohexylurea, N,N'-diethylurea, N-ethyl-N'-butylurea, N,N'-di-n-propylurea, N,N'-diisopropylurea, N,N'di-n-butylurea, N,N'-di-tertiary-butylurea, N,N'-dihexylurea, N,N'-diallylurea, N,N'-di-(3-methoxypropyl)-urea,N,N'-dicyclohexylurea, N,N'-dibenzylurea, N,N'-diphenyl-urea and the corresponding N,N'-disubstituted thioureas as well as dithiocarbamic acid salts of the general formula

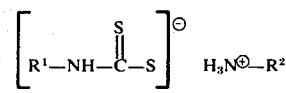

in which $R^1$ and $R^2$ can be the same or different and represent alkyl, cycloalkyl or aralkyl groups containing 1 to 10 carbon atoms.

The biuretizing agents preferably used for the process according to the invention are water, tertiary butanol and formic acid or mixtures of these components.

The addition of catalysts to accelerate the biuretization reaction as described in U.S. Pat. application Ser. No. 47,134 filed on June 17, 1970 is advisable especially when using tertiary alcohols as biuretizing agents. The preferred catalysts among those disclosed in said U.S. patent application are the ammonium resp. hydrazinium salts of primary, secondary or tertiary aliphatic amines the aliphatic radicals of which are alkyl radicals having 1 to 4 carbon atoms resp. of N,N-Dialkylhydrazine the alkyl radical of these compounds being aliphatic hydrocarbon radicals with 1 to 4 carbon atoms and mineral acids especially hydrogen halide acids preferably hydrochloric acid. When the process according to the invention is carried out with such catalysts and with a tert. alcohol as biuretizing agent using the particular ratio of dissocyanates to biuretizing agents which is an essential feature of the invention, the improved volume/time yields which are characteristic of the process of U.S. Pat. application Ser. No. 47,134 filed June 17, 1970 are obtained and at the same time the products obtained are substantially reduced in viscosity in accordance with the invention as compared with the biuret polyisocyanates known in the art.

The process according to the invention is basically carried out according to the known processes of the art such as those described, for example, in U.S. Pat. Nos. 3,124,605 and 3,358,010 or in U.S. Pat. application Ser. No. 47,134 filed on June 17, 1970 but the diisocyanates and biuretizing agents are used in proportions which correspond to a molar ratio of diisocyanate to monofunctional biuretizing agent of at least 11 : 1, preferably between about 12 : 1 and about 40 : 1 and in particular between about 12 : 1 and about 20 : 1. The process according to the invention is generally carried out at a temperature of from about 60° to about 250°C and preferably from about 85° to about 190°C. The reaction should generally be started at temperatures of about 85° to 100°C and completed at about 170° to 190°C. The termination of the reaction can easily be recognized by the cessation of the evolution of gas since the process according to the invention carried out with any of the biuretizing agents suitable for the invention is accompanied by the formation of by-products which are gaseous at the reaction temperatures employed. When water is used as the biuretizing agent, for example, carbon dioxide is formed as the gaseous by-product whereas when tertiary butanol is used, for example, isobutylene is formed in addition to carbon dioxide as gaseous by-product and when methylene is used, for example, the gaseous by-product formed is methyl isocyanate.

After termination of the biuretizing reaction, the excess diisocyanate is removed, preferably in a thin layer evaporator or by extraction with suitable solvents, e.g. n-hexane or n-heptane.

The biuretization reaction proceeds via the intermediate stage of a urea diisocyanate which is not isolated and from which the polyisocyanate with a biuret structure is subsequently formed. The process according to the invention for producing biuret polyisocyanates with substantially reduced viscosity can, therefore, be modified if desired in that the diisocyanates can be reacted with previously isolated urea diisocyanates instead of with the biuretizing agents mentioned above. In that case, isolated urea diisocyanates of the formula

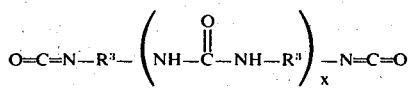

in which R³ represents the group obtained by the removal of the isocyanate groups from a diisocyanate and x denotes 1 or 2, are reacted with the quantities of diisocyanates indicated above preferably at 100° to 140°C, preferably using 12 to 20 mols of the monomeric aliphatic, cycloaliphatic or araliphatic diisocyanate.

According to one embodiment of the process of the invention, tertiary butanol, for example, is mixed in any proportions with water or with formic acid or with aqueous amines or hydrates of amines or with hydrazine hydrate in any concentrations so that the biuretizing components can be caused to act in various forms and concentration ratios on the diisocyanaes. In this variation of the process, it is frequently advantageous to add the above mentioned components in the vapour form or gaseous form because, in that case, only an extremely small concentration of biuretizing agent is introduced into the diisocyanate so that the formation of higher molecular weight diureas, triureas, tetraureas and in particular pentaureas, can be practically completely prevented.

The preferred biuretizing agents for this method of carrying out the process are mixtures of water and tertiary butanol at any concentrations, mixtures of water and formic acid and 1 : 1 : 1 mixtures of water, formic acid and tertiary butanol. Another biuretizing agent which has not previously been described and which is also suitable for these variations of the process is hydrazine hydrate or a mixture of hydrazine hydrate and tertiary butanol in a molar ratio of between 1 : 2 and 1 : 4. The biuret polyisocyanates thereby obtained contain hydrazodicarbonamide tetraisocyanates mixed with the products according to the invention in quantities depending on the quantity of hydrazine hydrate added. These hydrazodicarbonamide tetraisocyanates have the following idealized constitution:

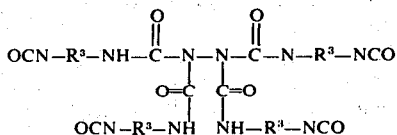

in which R³ has the meaning indicated above.

These hydrazodicarbonamide polyisocyanates make the products of the process extremely resistant to oxidation processes and lacquers etc. produced from products which contain these polyisocyanates have a substantially increased resistance to discoloration at temperatures of from 180° to 260°C.

Another variation of the process according to the invention consists in reacting dithiocarbamic acid salts with diisocyanates. The formation of biuret polyisocyanates by this reaction is accompanied by the splitting off of carbon oxysulphite and isothiocyanates. It has been found that, the same products are also obtained by using symmetrically N,N'-substituted thioureas. The reaction then takes place in accordance with the following overall equation:

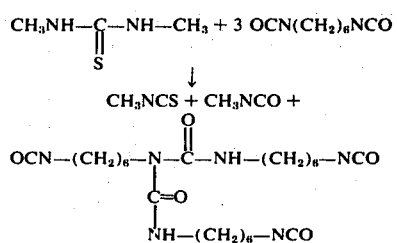

According to another new and very interesting variation of the process, which is particularly surprising in view of the known method of preparing biuret polyisocyanates by means of formic acid, the process of biuretization according to the invention is carried out under particular temperature conditions whereby biuretization is accompanied by the formation of N-formyl urea diisocyanates of the following constitution:

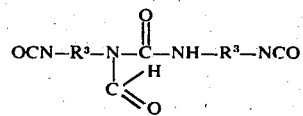

in proportions of 10 – 60 percent by weight, preferably 20 to 40 percent by weight. In this variation of the process according to the invention, formic acid or a mixture of formic acid and water (1 : 1) is reacted with diisocyanates at 95° to 110°C whereby the dehydrating effect of diisocyanates on formic acid in accordance with the equation

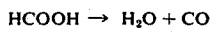

is strongly suppressed and substantial quantities of N-formylamide monoisocyanates of the above formula are obtained, in which formula R³ represents a group obtained by the removal of the isocyanate groups from a diisocyanate. These N-formylated urea diisocyanates are excellent reactive diluents for the biuret polyisocyanates formed at the same time and very considerably reduce their viscosity. The formation of difficulty soluble polyurea which occur as unwanted deposits in the upper part of the reaction vessel when biuret polyisocyanates are produced by reacting diisocyanates with water is thereby completely prevented.

Products with equally advantageous viscosity properties are also obtained according to the invention if formamide or N-substituted formamides are used as reactive, viscosity reducing additives. In that case, biuret polyisocyanates which contain formyl groups are obtained in accordance with the following constitutional formulae

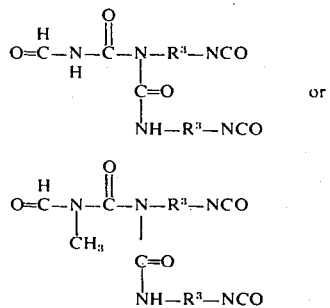

in which $R^3$ has the meaning specified above.

In this variation of the process, at least 11 mols of diisocyanate are reacted with 1 mol of formic acid. The reaction is preferably carried out using from 11 to 40 mols of diisocyanate to 1 mol of formic acid.

acid in vapor form is absorbed by suction at a reduced pressure of about 14 to 100 Torr in quantities of about 1 mol to 16 mols of diisocyanate over a period of 2 hours. This constitutes a particularly advantageous method of introducing a suitable proportion of formic acid for producing low viscosity biuret polyisocyanate mixtures. By this variation of the process it is possible to produce biuret polyisocyanates with a viscosity of 550 cP which contain about 30% by weight of formyl urea diisocyanate in solution as a valuable reactive diisocyanate and "liquidizer."

Primary amines such as methylamine, ethylamine, propylamine, tertiary butylamine, allylamine, butylamine, etc. can also be used as biuretizing compounds in the process according to the invention for producing biuret isocyanates with substantially reduced viscosity. According to the invention, these primary amines are used in proportions of about 1 mol to at least 11 mols and preferably about 12 to 20 mols of diisocyanate. In this case, a disubstituted urea isocyanate (III) is first formed from the diisocyanate (I) and any primary amine (II) according to the following reaction scheme given by way of example, and this disubstituted urea isocyanate (III) then reacts with a second molecule of diisocyanate (I) to form a trisubstituted biuret diisocyanate (IV). The trisubstituted biuret diisocyanate (IV) is then reacted with a third molecule of diisocyanate (I) at a higher temperature, whereby a monoisocyanate (V) is released and a urea diisocyanate is formed as an intermediate product which continues to react with the diisocyanate to form a polyisocyanate with a biuret structure (VI).

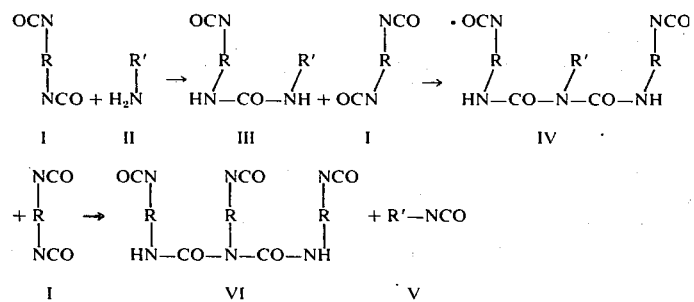

The reaction can also be carried out in the presence of solvents; these must not contain any hydrogen atoms which would react with isocyanate groups. Suitable solvents are, for example, chlorinated aliphatic and aromatic hydrocarbons, glycol monomethyl ether acetate and dioxane.

This variation of the process according to the invention in which formic acid or a mixture of formic acid and water, formic acid and tert.-butanol or tert.-butanol and formic acid, etc. is used makes it possible to produce products which have lower viscosities than could previously be obtained, e.g. viscosities of 550 to 950 cP/20°C.

Aqueous formic acid and formamide or hydrazine salts of formic acid can also be used. The reaction product can be modified by adding minor quantities of compounds with reactive hydrogen atoms such as diols, ureas or acid amides to the reaction mixture.

According to a particularly interesting variation of the process of biuretization with formic acid accompanied by the formation of N-formylurea diisocyanate as viscosity reducing and elasticizing diisocyanate, formic To maintain the reaction sequence in the direction indicated above it is necessary to ensure the continuous removal of the monoisocyanate formed. If the monoisocyanates are capable of being distilled, this continuous removal can be achieved by employing elevated temperatures and optionally reduced pressures or by using carrier gases.

Removal of the monoisocyanates can also be achieved by passing an inert carrier gas such as nitrogen through the reaction mixture during the decomposition reaction which takes place at elevated temperatures. This method is applicable in the case of low boiling aliphatic alkyl isocyanates with boiling point below 100°C.

Suitable primary monoamines are, for example methylamine ethylamine, propylamine, isopropylamine, butylamine, isobutylamine, tert.-butylamine dodecylamine, allylamine, 3-methoxypropylamine, cyclohexylamine, benzylamine, aniline, o-, m- and p toluidine, p-methoxyaniline and p-chloroaniline. Saturated alkylamines containing 1 to 6 carbon atoms are particularly preferred.

Masked primary monoamines can be used instead of the free amines, for example their salts with carbonic acid, formic acid, acetic acid, trichloroacetic acid or oxalic acid.

The process is carried out by adding a primary monoamine to the polyisocyanate in the proportions laid down by the invention. Since the reaction between the isocyanate and amine generally proceeds very rapidly and exothermically, it may be carried out at or below room temperature or, of course, at elevated temperatures. The amine is preferably introduced into the polyisocyanate in the gaseous state, preferably together with a carrier gas, such as nitrogen. The reaction between the amine and the polyisocyanate is completed as soon as the amine has been introduced. The product obtained depends on the quantities of reactants used; for example, the reactants can proceed to the formation of a urea isocyanate. If the total quantity of polyisocyanate required for the final equilibrium state is available, the reaction continues, especially if elevated temperatures are employed, so that with continuous decomposition and shift in the equilibrium, the aforesaid intermediate products give rise to monoisocyanates and biuret polyisocyanates with very reduced viscosity.

This last step of the process always takes place at an elevated temperature; e.g. at about 120° to 250°C. If the decomposition temperature, which naturally depends to a large extent on the constitution of the polyisocyanate and the amine, is employed from the very start, then the reaction proceeds smoothly through all its stages with immediate formation of the biuret polyisocyanates and the monoisocyanate. This method of operation is generally preferred.

The amine components used can also be ammonia, ammonium carbamate, urea or ammonium carbonate, in which case isocyanic acid is split off at a temperature of from about 190° to 200°C and again biuret polyisocyanate is obtained.

Another variation of the process according to the invention consists in using N,N'-disubstituted ureas of the type mentioned above by way of example, When these ureas are used as biuretizing agents, the gaeous by-products formed are the monoisocyanates which correspond to the N-substituents.

All the above mentioned variations of the reaction are generally carried out without solvent although inert solvents such as dioxane, tetrahydrofuran, triethylene glycol diacetate, toluene, benzene, chlorobenzene, o-dichlorobenzene, butyl acetate or ethylene glycol monoethyl ether acetate may be employed, if desired.

The polyisocyanates with biuret structure obtained by the process according to the invention are generally mixtures consisting of at least about 70% by weight of the tris-isocyanatobiuret compounds proper and not more than 30% by weight of higher molecular weight homologues or polyisocyanates which contain urea groups. No matter which diisocyanate is used in the process according to the invention, the biuret polyisocyanates obtained have much lower viscosities than the corresponding products obtained according to the known art. In general, the viscosity of the products of the process are always below 50,000 cP/20°C. Exceptionally low viscosity biuret polyisocyanates with viscosities below 4000 cP/20°C are obtained by using hexamethylene diisocyanate.

The products of the process are distinguished from the corresponding products of the known art also by their improved solubility and capacity for being diluted with the usual lacquer solvents and by their improved capacity for taking up pigments.

The products of the process are in principle suitable for any of the purposes for which biuret polyisocyanates are used. In particular they constitute valuable starting materials for the production and modification of synthetic resins by the isocyanate polyaddition process and those which are biuret derivatives of aliphatic, cycloaliphatic or araliphatic diisocyanates are also valuable starting materials for the production of light-fast lacquer coatings. One particularly advantageous characteristic of the products according to the invention is that they can be hardened by atmospheric moisture in the presence of catalysts to give rise to exceptionally elastic lacquers with maximum lightfastness without any addition of polyhydroxyl compounds and without any addition of solvents. They, therefore, constitute solvent-free single component systems with very good levelling flow properties.

The invention is further illustrated but is not intended to be limited by the following examples in which all parts and percentages are by weight unless otherwise specified.

EXAMPLE 1

(Comparison example in which the ratio between diisocyanate and biuretizing agent corresponds to the ratio of example 1 of U.S. Pat. No. 3,358,010)

a. 1000 Parts by weight of hexamethylenediisocyanate (5.952 mol) and 50 parts by weight of tert.-butyl alcohol (0.676 mol) are mixed at room temperature. The molar ratio is 8.8 mol of diisocyanate to 1 mol of tert.-butanol. The temperature of the reaction mixture is raised to 160°C over a period of about 30 minutes. Vigorous evolution of carbon dioxide and isobutylene sets in at this temperature. The temperature is then slowly raised to 185°C over a further 30 minutes. The evolution of gas ceases and hence the reaction is terminated after about 3 hours at 185°C. The reaction product is then freed from monomeric hexamethylene dissocyanate in a thin layer evaporator at a pressure of 0.2 Torr and a temperature of 160°C. Approximately 284 parts by weight of a viscous biuret polyisocyanate are obtained. Isocyanate content: 21.3 per cent by weight. The viscosity of the product is 5200 cP at 20°C.

b. If the 100 per cent biuret polyisocyanate prepared by this method is diluted with solvents such as
  a. ethyl acetate,
  b. toluene,
  c. xylene,
  d. xylene and ethyl acetate (1:1)
  e. xylene and butyl acetate or
  f. methyl ethyl ketone to produce 10% by weight solutions, the solutions become cloudy after only a few minutes. In all the samples a) to f) about 14 per cent by weight of the biuret polyisocyanate has settled as a ground sediment by the end of 4 hours. This sediment consists of difficulty soluble biuret polyisocyanates containing urea groups which have not been biuretized.

c. If 100 Parts by weight of the biuret polyisocyanate obtained in the above example are subject to fractiional precipitation at a constant temperature of 30°C by adding 100 Parts by weight of a mixture of 60 parts by weight of cyclohexane and 40 parts by weight of ethyl acetate three times and vigorously stirring the mixture and then leaving it to stand, then phase separation takes place. If the upper phase is removed each time and freed from cyclohexane and ethyl acetate, 48 per cent by weight of the biuret triisocyanate of the following constitution

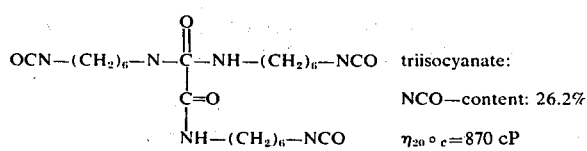

triisocyanate:
NCO—content: 26.2%
$\eta_{20°C} = 870$ cP can be isolated. The honey-like fraction which is insoluble in the mixture of cyclohexane and ethyl acetate contains 16 per cent by weight of a component which can be precipitated with toluene or ethyl acetate and which consists of polyisocyanates with urea groups which may be represented approximately by the following constitutional formula

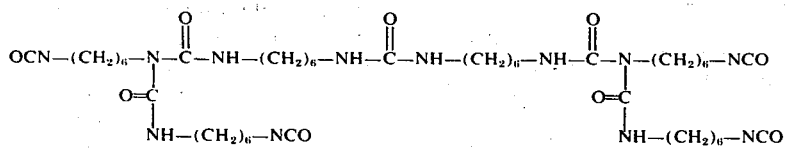

and which have an NCO content of about 18.1 per cent by weight and a viscosity which is no longer measurable at 20°C and 34 per cent by weight of a component which cannot be precipitated with toluene or ethyl acetate and which consists of higher molecular weight biuret polyisocyanates which are free from urea groups and corresponding approximately to the following constitutional formula

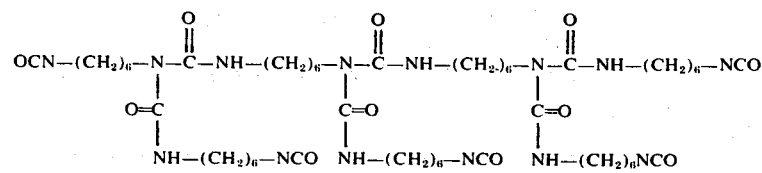

and have an isocyanate content of 19.3 per cent by weight and a viscosity of 16000 cP at 20°C.

This example shows clearly that the high viscosity of 5200 cP of the biuret polyisocyanate mentioned under a) is mainly due to the higher molecular weight biuret polyisocyanates.

EXAMPLE 2

(Process according to the invention)

If the quantity of diisocyanate used in the reaction according to the invention is increased by only about 2.2 mol, the viscosity is lowered very considerably and the biuret polyisocyanates become very much more easily miscible with solvents, as illustrated by the following example:

In this example 11 mol of hexamethylene diisocyanate (1848 parts by weight) are reacted with 1 mol of tert.-butyl alcohol (74 parts by weight) at 160° to 185°C as described in Example 1 a). When the biuret polyisocyanates are isolated as described in Example 1 a) the product obtained does not consist of higher molecular weight biuret polyisocyanates with increased viscosities and reduced solubility but surprisingly consists of a much less viscous biuret polyisocyanate with a viscosity of only 2800 cP at 20°C, i.e. the viscosity is reduced by about 47%. NCO content is 23.3 % by weight. This viscosity corresponds to a content of triisocyanate of about 70 % by weight 10% Solutions of the above mentioned low viscosity biuret polyisocyanate are remarkably stable when diluted with the lacquer solvents or solvent mixture indicated under (a) to (f) in Example 1(b). Whereas in Example 1 about 14 per cent by weight of difficulty soluble biuret polyisocyanates which contain urea groups are deposited after only 4 hours, the diluted solutions of Example 2 remain clear for 10 hours, an opalescent precipitate starts to form after a further 5 hours and only 4.6 per cent by weight of higher molecular weight biuret polyisocyanates which contain urea groups can be isolated after 48 hours.

EXAMPLE 3

The procedure is exactly the same as described in Example 1 (a) but hexamethylene diisocyanate and tert.-butyl alcohol are reacted in the following molar ratios:

a. 12 mol of hexamethylene diisocyanate and 1 mol of tert.-butyl alcohol
b. 15 mol of hexamethylene diisocyanate and 1 mol of tert.-butyl alcohol
c. 16 mol of hexamethylene diisocyanate and 1 mol of tert.-butyl alcohol
d. 17 mol of hexamethylene diisocyanate and 1 mol of tert.-butyl alcohol
e. 20 mol of hexamethylene diisocyanate and 1 mol of tert.-butyl alcohol.

The procedure is otherwise exactly the same as that described in Example 1. Low molecular weight mixtures with substantially increased concentrations of biuret triisocyanates are obtained. They have the following greatly reduced viscosities at 20°C.

a. 2560 cP NCO content: 23,49% (approx. content of triisocyanate: 72%)
b. 1350 cP NCO content: 24,05% (approx. content of triisocyanate: 82%)
c. 990 cP NCO content: 24,3% (approx. content of triisocyanate: >90%)

d. 885 cP NCO content: 24,5% (approx. content of triisocyanate: >90%)

e. 750 cP NCO content: 26,2% (theoretical value for triisocyanatohexylbiuret = 26.4%)

EXAMPLE 4

The procedure is exactly the same as that decribed in Example 1 (a) (12 mol of diisocyanate + 1 mol of tert.-butanol but 0.100 parts by weight of concentrated sulphuric acid is added as catalyst to the reaction mixture. Evolution of carbon dioxide already sets in at 70°C. The process is carried out as described in Example 2 at a temperature of 175°– 180°C and a slightly deeper colored biuret polyisocyanate is obtained which has a viscosity of 2750 cP at 20°C.

EXAMPLE 5

The procedure is exactly the same as that described in Example 1 (a) but 15 mol of hexamethylene diisocyanate are reacted with 1 mol of tert.-butanol in o-dichlorobenzene in 70% solution. The product is treated in a thin layer evaporator as described in Example 2 and a yellowish biuret polyisocyanate is obtained which has a viscosity of 1320 cP at 20°C and dilution properties as good as those of the product described in Example 2.

EXAMPLE 6 a. 15 Mol of hexamethylene diisocyanate are reacted with 1 mol of 3-methyl-3-pentanol as described in Example 1 a). A low viscosity biuret polyisocyanate is obtained after removal of the monomer at 0.2 Torr and 164°C. The viscosity of this fluid product is 1350 cP at 20°C. Isocyanate content: 23.9%; yield: 470 parts by weight.

b. The procedure is the same as described under a) and 3 mol of 1,2-di-(isocyanatomethyl)-cyclobutane are reacted with 0.2 mol of tert.-butanol in a molar ratio of 15 : 1. An extremely low viscosity biuret polyisocyanate is obtained which has an isocyanate content of 25.9% and a viscosity of 890 cP at 20°C.

EXAMPLE 7

The procedure is the same as that described in Example 1 a) but a tert.-alcohol of the following formula

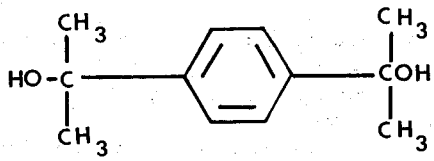

is used as biuretizing agent and 7.5 mol of hexamethylene diisocyanate are reacted with 0.25 mol of the above mentioned bis-carbinol.

The biuret polyisocyanate obtained after removal of the monomer as described in Example 1 has a viscosity of 1200 cP at 20°C. Isocyanate content 22.8%; yield 233 parts by weight.

EXAMPLE 8

37 Parts by weight of tert.-butanol alcohol (0.5 mol) are in each case mixed with 1260 parts by weight of hexamethylene diisocyanate (7.5 mol) (molar ratio 15 : 1). About 2.5 parts by weight of N,N-dimethylhydrazine are added dropwise to this mixture with rapid stirring. The following compounds are added to these solutions:

a. 1.12 parts by weight of dimethylammonium chloride
b. 1.2 parts by weight of N,N-dimethylhydrazinium chloride
c. 1.52 parts by weight of diethylammonium chloride
d. 2.28 parts by weight of di-n-butylammonium chloride
e. 3.2 parts by weight of dimethylbenzylammonium chloride
f. 1.8 parts by weight of morpholine hydrochloride.
g. 1.9 parts by weight of piperidine hydrochloride The reaction mixtures are heated in each case to a reaction temperature of 185°C and the quantity of carbon dioxide and isobutylene liberated is determined with a gas meter. In all the experiments (a) to (g) the evolution of gas and formation of biuret polyisocyanate is completed by the end of 50 minutes whereas the non-catalyzed reaction results in only 90% conversion after 3 hours. The biuret polyisocyanates obtained after removal of the monomer (in a thin layer evaporator at 0.2 Torr and 162°C.), have the following viscosities and isocyanate contents:

a. 1390 cP/20°C; isocyanate content: 26.1%; yield: 235 parts by weight
b. 1420 cP/20°C; isocyanate content: 25.9%; yield: 233 parts by weight
c. 1350 cP/20°C; isocyanate content: 26.15%; yield: 234 parts by weight
d. 1450 cP/20°C; isocyanate content: 25.83%; yield: 235 parts by weight
e. 1490 cP/20°C; isocyanate content: 25,58%; yield: 233 parts by weight
f. 1320 cP/20°C; isocyanate content: 25.99%; yield: 235 parts by weight
g. 1358 cP/20°C; isocyanate content: 25.48%; yield: 235 parts by weight The biuret polyisocyanate prepared in experiment a) (isocyanate content 26.1%, $\eta_{20°C} = 1390$ cP) can be converted into a highly cross-linked lacquer film by stoving it for only a few seconds at a temperature of 230°C with a polyester polyol of phthalic acid anhydride and trimethylolpropane which has an hydroxyl content of about 8.5%.

EXAMPLE 9

The procedure is exactly the same as in Example 8 but the catalyst used is a mixture of 0.3 parts by weight of dimethylammonium chloride, 0.5 parts by weight of N,N-dimethylhydrazinium chloride and 1.5 parts by weight of dimethylcarbamic acid chloride and the reaction is carried out at a temperature of 165°C.

Here again the decomposition of tert.-butylurethane is found to take place much more rapidly than in the comparison experiment carried out without catalyst and again a biuret polyisocyanate with greatly reduced viscosity and high resistance to discoloration on heating is obtained. When the product is stoved with polyhydroxyl compounds, practically colorless lacquers with maximum lightfastness and gloss retention are obtained. $\eta_{20°C} = 1337$ cP; Isocyanate content 26.15%; yield 234.5 parts by weight.

Non-pigmented stoving lacquers produced from the biuretpolyisocyanate of Example 9 remain colorless for a long time when exposed to 220°C whereas biuret polyisocyanates which have been prepared without catalyst have a brown tinge after they have been stoved with polyhydroxyl compounds.

EXAMPLE 10

The procedure is the same as in Example 8 but the following polyisocyanates and catalyst mixtures are used for 18.5 parts by weight of tert.-butyl alcohol (0.25 mol):

a. 666 parts by weight of 3,3,5-trimethyl-5-isocyanatomethylcyclohexylisocyanate (3 mol), 1.8 parts by weight of triethylammonium chloride and 1 part by weight of ethyl hydrazinium chloride;
b. 666 parts by weight of 3,3,5-trimethyl-5-isocyanatomethylcyclohexylisocyanate (3mol), 78 parts by weight (about 0.2 mol) of a polyisocyanate of 1 mol of N,N-dimethylhydrazine and 2 mols of hexamethylenediisocyante, 1.8 parts by weight of diethyl ammonium hydrochloride and 0.5 parts by weight of triethyl ammonium formate;
c. 564 parts by weight of m-xylylene diisocyanate (3 mol), 1.9 parts by weight of hydrazinocarboxylic acid ethyl ester hydrochloride and 1.8 parts by weight of N,N-bis-($\beta$-hydroxyethyl)-hydrazinium chloride;
d. 564 parts by weight of m-xylylene diisocyanate (3 mol), 1.5 parts by weight of n-butylammonium chloride and 0.9 parts by weight of the salt of dimethylamine and phosphorous acid;
e. 540 parts by weight of 1-methyl-2,4-diisocyanatocyclohexane (3 mol), 2.1 parts by weight of hydrazinium chloride, 1.8 parts by weight, of the oxalate of N,N'-diaminopiperazine and 0.4 parts by weight of the carbamic acid chloride of 1 mol of hexamethylenediisocyanate and 2 mols of hydrogen chloride;
f. 540 parts by weight of 1-methyl-2,4-diisocyanatocyclohexane (3 mol) and 0.4 parts by weight of trimethylammonium chloride dissolved in 2 parts by weight of benzoyl chloride;
g. 498 parts by weight of 1,2-di-(isocyanatomethyl)-cyclobutane (3 mol) and 3 parts by weight of dimethylcarbamic acid chloride containing 8% of dimethylammonium chloride and 5% of phosgene;
h. 504 parts by weight of hexamethylene diisocyanate (3 mol), 1.5 parts by weight of dimethylammonium chloride and 6 parts by weight of N-N-dimethylhydrazine;
i. 504 parts by weight of hexamethylene diisocyanate (3 mol), 72 parts by weight (about 0.2 mol) of a polyisocyanate of 1 mol of N,N-dimethylhydrazine and 2 mols of hexamethylene diisocyanate, and 1.4 parts by weight of dimethyl ammonium chloride.

The following reaction times and viscosities are found after approximately 96% conversion to biuret polyisocyanates:

| Experiment | Reaction Time in minutes at 165°C in the presence of catalysts | Viscosity at 20°C |
|---|---|---|
| a) | 186 | 35000 cP (as compared with 95000 at a molar ratio of 6 : 1) |
| b) | 177 | 36700 cP |
| c) | 171 | 25000 cP |
| d) | 183 | 25800 cP |
| e) | 192 | 23900 cP |
| f) | 187 | 22500 cP |
| g) | 171 | 940 cP (as compared with 8500 at a molar ratio of 6 : 1) |
| h) | 168 | 1480 |
| i) | 167 | 1320 |

EXAMPLE 11

About 2560 Parts by weight of hexamethylene diisocyanate (15.2 mol) were reacted with 18 parts by weight of water (1 mol) over a period of 6 hours at 97° to 99°C with vigorous stirring. Only minor quantities of insoluble urea diisocyanates (>1%) have formed by the time all the water has been added. The temperature is maintained at 120°C for one hour. The filterd solution which is now clear is freed from monomeric hexamethylene diisocyanate by evaporation at 0.2 mm Hg and 160°C. Approximately 460 parts by weight of a biuret polyisocyanate which has a viscosity of 1480 cP at 20°C and an NCO content of 25.9% are obtained.

EXAMPLE 12

(Comparison example)

The procedure is exactly the same as described in Example 11 of U.S. Pat. Nos. 3,124,605 and 2560 parts by weight of hexamethylene diisocyanate (15.2 mol) are reacted with 56 parts by weight of water 3.1 mol). The yield of biuret polyisocyanates purified by thin layer evaporation is 1165 parts by weight. Whereas the biuret polyisocyanates prepared according to Example 11 by the process according to the invention have a viscosity of only 1480 cP at 20°C, the biuret polyisocyanate prepared according to U.S. Pat. No. 3,124,605 has a viscosity of 12500 cP at 20°C.

EXAMPLE 13

(Practical example of application)

About 20 mg. of a zinc salt of 2-ethylcaproic acid are added to 10 parts by weight of the biuret polyisocyanate prepared as described in Example 11, which has a viscosity of only 1480 cP. This low viscosity polyisocyanate can easily be cast on any substrate. When it is cast on glass substrates it flows smoothly without requiring the addition of any solvent. The lacquer undergoes cross-linking by reaction of the isocyanate groups with moisture to produce a surprisingly elastic and flexible lacquer film. Films formed from biuret polyisocyanates which have been prepared according to Example 12, on the other hand, flow unevenly and with difficulty and form deep craters, and satisfactory lacquer films can only be obtained with the addition of solvents.

EXAMPLE 14

In this example there is described the preparation of a biuret polyisocyanate mixture containing aromatic and aliphatic substituents, which is substantially reduced in viscosity by the procedure according to the invention.

About 2560 Parts by weight of hexamethylene diisocyanate (15.2 mol) and 174 parts by weight or tolylene-2,4 -diisocyanate (1 mol) are reacted with 18 parts by weight of water exactly as described in Example 11 but the water is absorbed into the reaction vessel in the form of steam by suction under vacuum at a temperature of 95°C over a period of 5 hours. This procedure produces clear solutions which give rise to fluid biuret polyisocyanates after removal of the monomer in a thin layer evaporator. Viscosity: 1700 cP at 20°C. If, on the other hand, the procedure described in U.S. Pat. No. 3,124,605 is employed, for example using the proportions indicated in Example 1 of the said patent, i.e. diisocyanate and water in a molar ratio of about 5 : 1, then the biuret polyisocyanates obtained are no longer easily fluid and have viscosities above 120000 cP at 20°C.

EXAMPLE 15

About 17 parts by weight (0.5 mol) of hydrogen sulphide which has been dried over calcium chloride are introduced into 1680 parts by weight (10 mol) of freshly distilled hexamethylene diisocyanate at a rate of about 3 liters per hours while the hexamethylene diisocyanate is kept at a temperature of about 97°C. When all of the hydrogen sulphide has been added, the reaction mixture is stirred at 140°C for 3 hours and then freed from monomeric hexamethylene diisocyanate in a thin layer evaporator. An extremely low viscosity biuret polyisocyanate free from monomer is obtained. It has a viscosity of 815 cP at 20°C, whereas a biuret polyisocyanate prepared by the procedure described in Example 2 of German Patent Specification No. 1,165,580 has a viscosity of 11900 cP at 20°C.

EXAMPLE 16

This example shows a particularly advantageous method of biuretization and preparation of biuret polyisocyanates with substantially reduced viscosity by reacting various aliphatic, cycloaliphatic and araliphatic diisocyanates with steam at reduced pressure.

About 15 mol of the following diisocyanates;
a. hexamethylene diisocyanate,
b. m-xylylenediisocyanate,
c. 1-isocyanato-3,3,5-trimethyl-5-isocyanatomethylcyclohexane (isophorone diisocyanate)

are in each case heated to 99°C and kept at a pressure of 99 Torr with vigorous stirring. The reaction vessel is connected to a flask which contains 18 parts by weight of water (1 mol). Water is slowly absorbed from the flask in the form of steam in the course of 7 hours. After purification by thin layer evaporation, biuret polyisocyanates with substantially reduced viscosity are obtained without any deposition of polyurea. The viscosities are as follows:

a. $\eta_{20°C} = 1\,150$ cP b. $\eta_{20°C} = 39\,500$ cP c. $\eta_{20°C} = 33200$ cP

EXAMPLE 17

This example describes under a) to i) methods of carrying out the process according to the invention using substances which split off water and mixtures of tertiary butanol, water and formic acid to produce biuret polyisocyanates.

About 2560 Parts by weight of hexamethylene diisocyanate (15.2 mol) are in each case reacted with one of the following reactants at 96° to 97°C:
a. Chloral hydrate (1 mol)
b. salicylic acid (1 mol)
c. formic acid (1 mol)
d. $Na_2SO_4 \cdot 10\,H_2O$ (0.1 mol)
e. $NH_2-NH_2 \cdot H_2O$ (0.5 mol)
f. water (0.33 mol), tert.-butanol (0.33 mol), formic acid (0.33 mol); total 1 mol
g. $H_3PO_4 \cdot H_2O$
h. $H_3PO_3 \cdot H_2O$
i. 200 Parts by weight of silicic acid containing approximately 18 parts by weight of bound water.

The process is carried out as described in Example 11. Insoluble constituents such as sodium sulphate, silicic acid and syrupy polymeric polyphosphoric acids are removed by filtration and the biuret polyisocyanates are purified in a thin layer evaporator at 0.2 Torr and 163°C. Biuret polyisocyanates and modified biuret polyisocyanates with substantially reduced viscosities are obtained. The viscosities, isocyanate contents and yields are indicated below:

a. $\eta_{20°C} = 1200$ cP; isocyanate content: 26.2%; yield: 468 parts by weight
b. $\eta_{20°C} = 1400$ cP; isocyanate content: 24.6%; yield: 480 parts by weight
c. $\eta_{20°C} = 850$ cP; isocyanate content: 26.1%; yield: 465 parts by weight
d. $\eta_{20°C} = 1250$ cP; isocyanate content: 25.2%; yield: 455 parts by weight
e. $\eta_{20°C} = 2300$ cP; isocyanate content: 27.2%; yield 806 parts by weight
f. $\eta_{20°C} = 1035$ cP; isocyanate contents: 26.3%; yield: 463 parts by weight
g. $\eta_{20°C} = 1250$ cP; isocyanate content: 25.2%; yield 470 parts by weight
h. $\eta_{20°C} = 1300$ cP; isocyanate content: 26.1%; yield: 465 parts by weight
i. $\eta_{20°C} = 1035$ cP; isocyanate content: 26.3% yield: 430 parts by weight

EXAMPLE 18

The procedure described here illustrates a new method of biuret polyisocyanate preparation with the simultaneous formation of alkyl isothiocyanates, monoisocyanates and carbon oxysulphide and can be applied to any dithiocarbamic acid salts of substituted monoamines and carbon disulphide.

About 0.25 Mol of a suspension of

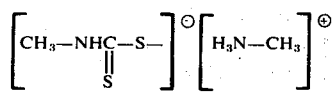

in o-dichlorobenzene is added to 1008 parts by weight of hexamethylene diisocyanate (6 mol) after replacement of all the atmospheric oxygen with nitrogen, and the mixture is slowly heated to 120°C. Carbon oxysulfide begins to split off and the dithiocarbamic acid salt goes into solution. The temperature is raised to 180°C over a period of 3 hours, a stream of nitrogen free from oxygen is passed through the reaction vessel while biuretization is carried out, and the methyl isothiocyanate and methyl isocyanate split off are condensed in three cooling traps connected in series. The cooling traps are then replaced by fresh cooling traps and the reaction to split off the monisocyanate and monothiocyanate mixture is completed at 200 Torr and 160°C. The yield of methyl thiocyanate and methyl isocyanate mixture is 92% of the thoery, based on the quantity of dithiocarbamic acid salt put into the reaction.

The product is freed from monomer and processed as described in Example 2. The biuret polyisocyanates obtained have a much lower viscosity than those obtained by known processes. Isocyanate content: 25.3%; viscosity 1150 cP at 20°C; yield: 232 parts by weight.

EXAMPLE 19

About 1008 Parts by weight of hexamethylene diisocyanate (6 mol) are heated to 60°C while the atmospheric oxygen dissolved in it is continuously removed by a anhydrous stream of nitrogen. 23 Parts by weight of anhydrous formic acid (0.5 mol) are then absorbed by suction at a vacuum of 14 Torr from a flask attached to the stirrer apparatus over a period of 2 hours. The reaction mixture is then stirred for one hour, during which time all the carbon dioxide is released from the reaction mixture. The temperature is then raised to 85°C, and during this second stage about 6.5 liters of carbon monoxide are liberated. The liberation of carbon monoxide is completed by stirring at 120°C.

Monomeric diisocyanate is removed from the biuret polyisocyanate mixture by repeated extraction of the reaction mixture with n-hexane (4 times). The biuret polyisocyanate obtained after removal of the extractant has an extremely reduced viscosity and contains about 42% by weight of N-formylurea diisocyanate of the following constitution

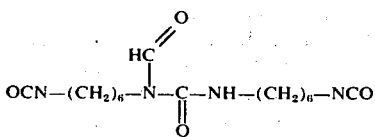

Yield: 376 parts by weight: Isocyanate content: 24.8%; viscosity: 850 cP at 20°C.

EXAMPLE 20

The procedure is the same as that described in Example 19 using 6 mols of hexamethylene diisocyanate and, in each case, 0.5 mol of one of the following compounds as biuretizing agent, i.e. biuretization is carried out at a molar ratio of 12 : 1.

a. 22.5 parts by weight of formamide
b. 8.5 parts by weight of gaseous ammonia
c. 15.5 parts by weight of gaseous methylamine
d. 44 parts by weight of N,N'-dimethylurea.

Biuretization is first carried out at 140°C under nitrogen as protective and propellant gas, and the temperature is then raised to 180°C and in experiments c) and d) methyl isocyanate is condensed in cooling traps at −80°70°C and 200 mm Hg. Heating is continued for a further 1½ hours at 200°C, isocyanic acid being split off in experiments a) and b). The biuretized solutions are then freed from monomeric hexamethylene diisocyanate in a thin layer evaporator at 0.15 Torr. Extremely low viscosity biuret polyisocyanates are obtained which have the following isocyanate contents and the following viscosities at 20°C:

a. Isocyanate content: 29.88%; 715 cP/20°C
b. Isocyanate content: 29.35%; 680 cP/20°C
c. Isocyanate content: 29.13%; 816 cP/20°C
d. Isocyanate content: 26.2%; 890 cP/20°C When procedures a) and b) are compared with the procedure described in U.S. Pat. No. 3,284,479 (Example 10: viscosity 1590 cP/20°C) it is found that the viscosity of the products obtained by procedures a) and b) are lower by about 875 cP to 910 cP. When procedure c) is compared with the procedure described in U.S. Pat. No. 3,392,183 (Example 7: viscosity 12900 cP/20°C) the viscosity is found to be extremely reduced by procedure c), namely by about 12084 cP. Procedure d) results in a substantial reduction in viscosity compared with the procedure described in U.S. Pat. No. 3,367,956 (Example 2: viscosity 2500 cP/20°C), namely by about 1610 cP.

EXAMPLE 21

About 322 parts by weight (1 mol) of the sparingly soluble urea diisocyanate of the following constitution

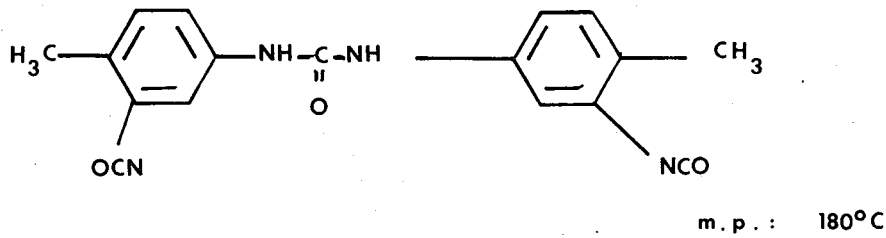

m.p.: 180°C obtained from tolylene-2,4-diisocyanate and water are heated to 140°C in 3360 parts by weight (20 mol) of hexamethylene diisocyanate under a stream of nitrogen gas for 5 hours. The sparingly soluble urea diisocyanate dissolves. After removal of the monomeric hexamethylene diisocyanate, a yellowish biuret polyisocyanate which contains both aromatic and aliphatic groups in the same molecule and corresponds to the following idealized formula

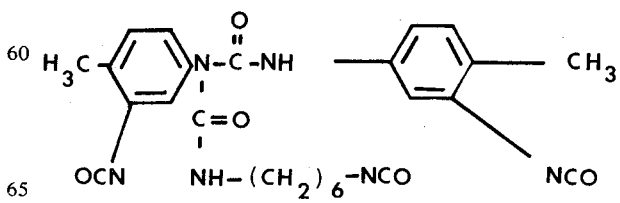

is obtained in quantitative yield. Due to the procedure according to the invention, the biuret polyisocyanate has excellent stability in ethyl acetate. 10 solutions of this triisocyanate, which is a soft resin, are completely stable over a tested period of 6 months and have no tendency to deposit sparingly soluble biuret polyisocyanates containing urea groups which have not been biuretized.

EXAMPLE 22

(Practical example of application)

About 100 Parts by weight of a polyester of 3 mols of phthalic acid and 4 mols of trimethylolpropane (10.1% OH) are made up into a paste with 100 parts by weight of a mixture of equal parts of toluene, ethyl acetate and glycol monomethyl ether acetate and 105 parts by weight of titanium dioxide (rutile type). An additional 179 parts by weight of the solvent mixture and 2 parts by weight of polyvinylmethyl ether are added to this paste. Any of the low viscosity biuret polyisocyanates according to the invention described in the above examples can be added to the resulting pigmented mixture as cross-linking agent without any further addition of solvent to effect cross-linking of the polyesters at an NCO/OH ratio of 1 : 1 without any premature precipitation, phase separation or formation of concentrate, etc. being observed. These mixtures have a sufficiently long pot life. The lacquer solutions can be applied to any substrates and result in very stable elastic lacquers after drying. If 0.1 parts by weight of a tin-II salt of 2-ethylcaprioc acid or of a zinc-II salt of 2-ethylcaproic acid are added to the lacquer mixtures, the lacquers obtained are hard, scratch-resistant and resistant to solvents such as toluene after only 24 hours. They show no signs of yellowing when exposed to artificial or natural light and have excellent gloss retention.

EXAMPLE 23

(Practical example of application)

About 75 percent of weight solutions in ethyl glycol ether acetate and methyl ethyl ketone (1 : 1) of a polyester of phthalic acid and trimethylolpropane which has a hydroxyl group content of 8.5% are slightly diluted with the biuret polyisocyanate prepared according to Example 17 (f) (26.3% NCO content, 80 parts by weight) to form a two-component clear lacquer solution which has excellent flow and does not become cloudy. If 0.050 parts by weight of zinc salt of 2-ethyl-caproic acid is added as catalyst to this mixture and thin layers of this mixture are applied to surfaces, hard, glossy, clear lacquer films which do not undergo yellowing in the light are obtained over a period of 24 hours at room temperature.

EXAMPLE 24

(Practical example of application)

a. About 200 Parts by weight of a hexanediol polycarbonate (hydroxy number 56) or 168 parts by weight of a polyester of adipic acid, neopentyl glycol, hexanediol and 1,4-butylene glycol (ratio of diols 1 : 1 : 1) and 200 parts by weight of a polyester of adipic acid and butane-1,4-diol which has a hydroxyl number of 54 are mixed with 300 parts by weight of the low viscosity biuret polyisocyanate described in Example 2 (isocyanate content 23.3%) at 75°C. Premature cross-linking does not occur. Mixtures of isocyanate prepolymers are formed by reaction of the linear hydroxyl polyesters with the biuret polyisocyanates which are present in excess. Isocyanate content of the prepolymer mixture: 6.3% b. The solvent-free melts of the isocyanate prepolymer mixtures with excess biuret polyisocyanates can be used to produce highly elastic coatings on any substrates and these coatings can be cross-linked by moisture. They have a rubbery elastic character and excellent lightfastness.

c. If ε-cparolactam, methyl ethyl -caprolactam, or phenol is added to the above mentioned mixtures of biuret polyisocyanates and isocyanate prepolymers without solvents a slow reaction takes place to form the corresponding masked isocyanates. When these masked isocyanates which melt at 90°C and then can easily be spread-coated are applied to substrates and cross-linked with moltent trimethylolpropane, elastic, rubber-like coatings are obtained.

What is claimed is:

1. In the production of a polyurethane resin wherein a polyisocyanate is reacted with an active hydrogen containing material, the improvement wherein said polyisocyanate has a biuret structure and a maximum viscosity of 50,000 cP at 20°C. and is produced by a process comprising:

A. reacting (1) excess quantities of an organic diisocyanate having aliphatically bound isocyanate groups with (2) a biuretizing agent selected from the group consisting of water and organic compounds which convert organic isocyanates into the corresponding biurets at elevated temperatures, the substituents of said organic compounds being inert in the biuretization process and not forming a constituent of the biuret, at a temperature of from 60° to 250°C, and B. removing excess unreacted diisocyanate, said process characterized in that the organic diisocyanate and biuretizing agent are used in proportions corresponding to a molar ratio of diisocyanate to monofunctional biuretizing agent of at least 11:1.

2. The process of claim 1, wherein the organic diisocyanate is hexamethylene diisocyanate.

3. The process of claim 1, characterized in that the biuretizing agent used for the biuretizing reaction comprises formic acid and the reaction temperature is kept at 60° to 120°C; whereby N-formylated urea diisocyanates, which substantially reduce the viscosity, are obtained in addition to the biuret polyisocyanate.

4. The process of claim 1, characterized in that the biuretizing agent used is a tertiary monoalcohol.

5. The process of claim 4, characterized in that the tertiary alcohol used is tert.-butanol.

* * * * *

REEXAMINATION CERTIFICATE (181st)
United States Patent [19]

[11] B1 3,976,622

Wagner et al.

[45] Certificate Issued Mar. 27, 1984

[54] PROCESS FOR THE PRODUCTION OF POLYISOCYANATES WITH A BIURET STRUCTURE

[75] Inventors: Kuno Wagner; Johannes Eimer; Joachim Zirner, all of Leverkusen; Rainer Raab, Odenthal; Dietrich Liebsch, Leverkusen, all of Fed. Rep. of Germany

[73] Assignee: Bayer Aktiengesellschaft, Leverkusen, Fed. Rep. of Germany

Reexamination Request:
No. 90/000,334, Mar. 1, 1983

Reexamination Certificate for:
Patent No.: 3,976,622
Issued: Aug. 24, 1976
Appl. No.: 578,557
Filed: May 19, 1975

Related U.S. Application Data

[62] Division of Ser. No. 441,778, Feb. 12, 1974, Pat. No. 3,903,127.

[30] Foreign Application Priority Data

Feb. 17, 1973 [DE] Fed. Rep. of Germany ....... 2308015

[51] Int. Cl.$^3$ .............................................. C08G 18/79
[52] U.S. Cl. ....................................... 528/67; 528/81; 528/83

[56] References Cited

U.S. PATENT DOCUMENTS

| | | | |
|---|---|---|---|
| 3,124,605 | 3/1964 | Wagner | 260/453 |
| 3,201,372 | 8/1965 | Wagner | 260/77.5 |
| 3,350,438 | 10/1967 | Hennig | 521/162 |
| 3,358,010 | 12/1967 | Britian | 260/453 |

OTHER PUBLICATIONS

Wagner, Kuno, "Niedermolekulare Polyisocyanate mit Biuret Struktur", *Angew. Chem.* 74, No. 21, pp. 799–801 (1962).
Principles of Polymerization–2nd Edition. Interscience 1981, pp. 22–25.
Encyclopedia of Polymer Science & Technology, vol. 9, pp. 182–189, Interscience Publishers.

*Primary Examiner*—Maurice J. Welsh

[57] ABSTRACT

Comparatively low viscosity biuret containing polyisocyanates are produced by reacting diisocyanates and biuretizing agents in proportions corresponding to a molar ratio of diisocyanate to monofunctional biuretizing agent of at least 11:1.

; # REEXAMINATION CERTIFICATE ISSUED UNDER 35 U.S.C. 307.

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 2 and 3, having been finally determined to be unpatentable, are cancelled.

Claim 1 is determined to be patentable as amended:

Claims 4 and 5, dependent on amended claims, are determined to be patentable.

1. In the production of a polyurethane resin wherein a polyisocyanate is reacted with an active hydrogen containing material, the improvement wherein said polyisocyanate has a biuret structure and a maximum viscosity of 50,000 cP at 20° C. and is produced by a process comprising
   A. reacting (1) excess quantities of [an organic] *hexamethylene* diisocyanate [having aliphatically bound isocyanate groups] with (2) a biuretizing agent selected from the group consisting of water and organic compounds which convert organic isocyanates into the corresponding biurets at elevated temperatures, the substituents of said organic compounds being inert in the biuretization process and not forming a constituent of the biuret, at a temperature of from 60° to 250° C., and
   B. removing excess [unreacted] *hexamethylene* diisocyanate, said process characterized in that the [organic] *hexamethylene* diisocyanate and biuretizing agent are used in proportions corresponding to a molar ratio of diisocyanate to monofunctional biuretizing agent of at least 11:1.

* * * * *